United States Patent [19]

Bils

[11] 4,202,289
[45] May 13, 1980

[54] SPECIMEN PROCESSING APPARATUS FOR MICROSCOPY

[76] Inventor: Robert F. Bils, 816 Westmoreland Dr., Montebello, Calif. 90640

[21] Appl. No.: 923,099

[22] Filed: Jul. 10, 1978

[51] Int. Cl.² ............................................. C23C 13/08
[52] U.S. Cl. .................................. 118/50; 8/94.1 R; 8/94.11; 118/423; 118/425; 118/428; 118/500; 134/110; 134/117; 134/137; 134/143; 134/201
[58] Field of Search ............... 118/500, 423, 425, 428, 118/50; 134/117, 110, 137, 201, 143; 8/94.11, 94.1 R

[56] References Cited
U.S. PATENT DOCUMENTS

| | | | |
|---|---|---|---|
| 2,837,055 | 6/1958 | Whitehead | 118/500 |
| 3,167,079 | 1/1965 | Weil | 134/137 |
| 3,168,100 | 2/1965 | Rich | 134/137 |
| 3,809,008 | 5/1974 | Takahashi | 118/50 X |

Primary Examiner—Bernard D. Pianalto
Attorney, Agent, or Firm—William H. Maxwell

[57] ABSTRACT

A manually operable apparatus for preparing specimens to be viewed microscopically, and providing resuable parts and elements selectively employed to immerse the specimens for fixation, staining, etc. for dehydration and embedding, comprising at least one sieve cup and tube combination to be arranged in a base and oriented by a stripper plate for transport by a header, and adapted to immersion in a vessel requiring a low level of solution for specimen treatment therein.

41 Claims, 9 Drawing Figures

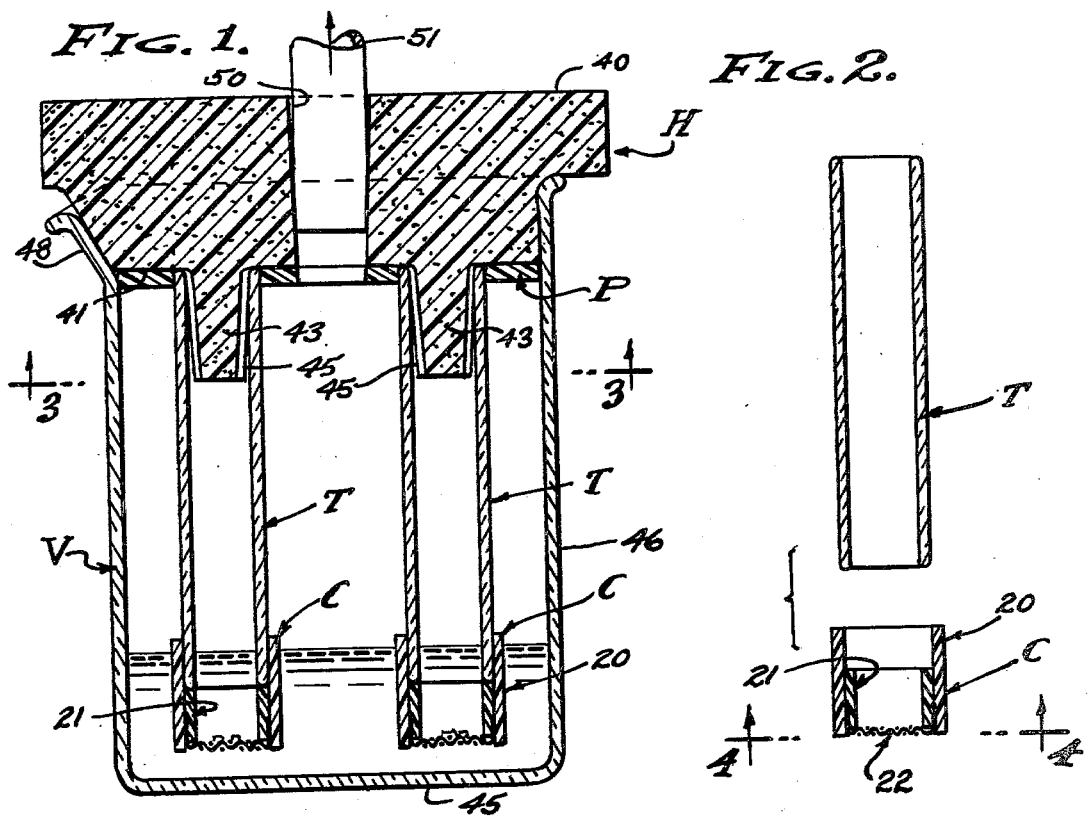
FIG. 1.
FIG. 2.
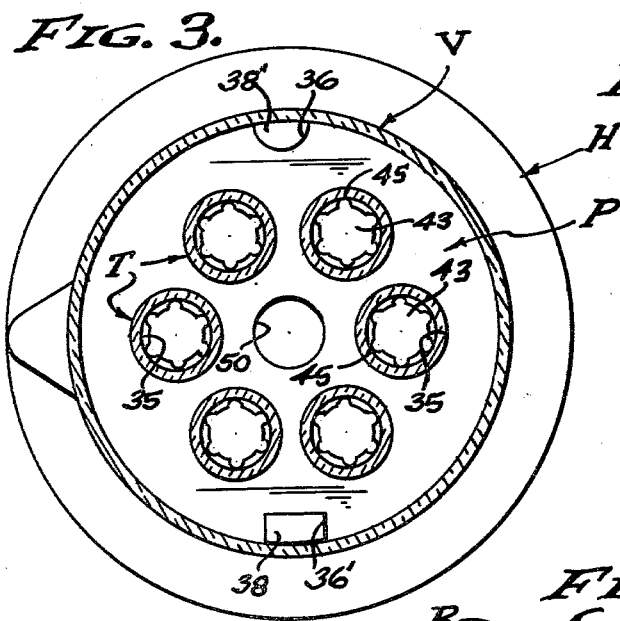
FIG. 3.
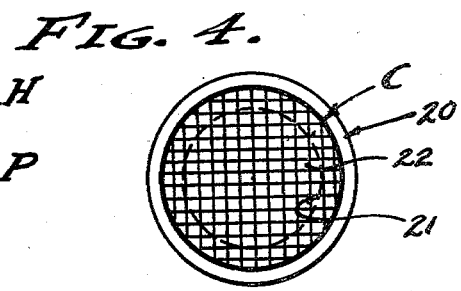
FIG. 4.
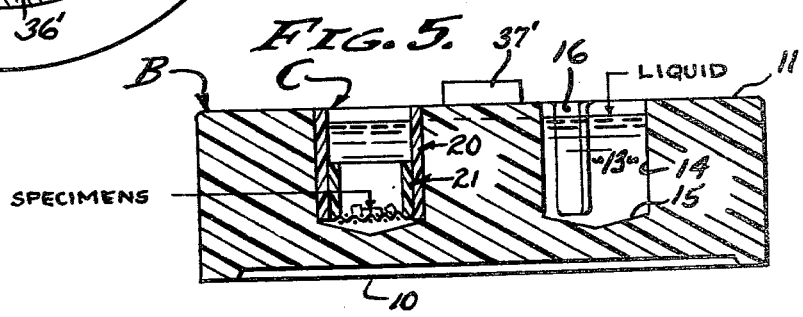
FIG. 5.

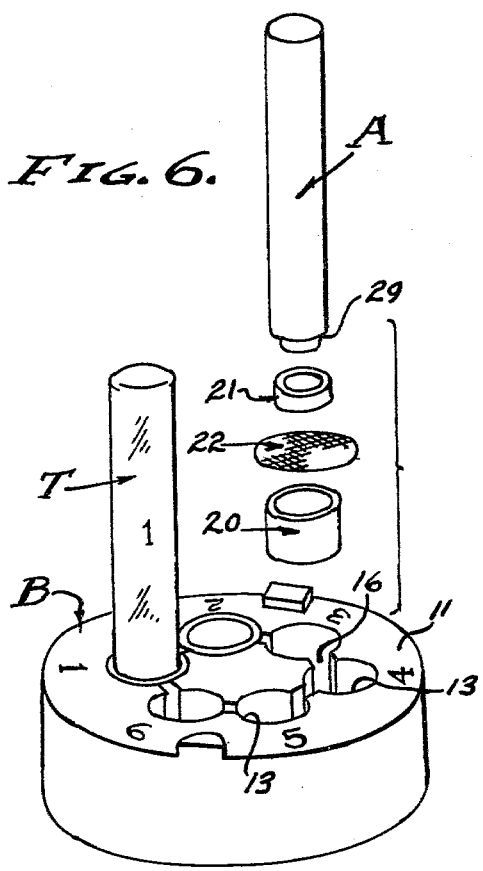

SPECIMEN PROCESSING APPARATUS FOR MICROSCOPY

BACKGROUND

Specimens must be specially prepared for viewing with the electron microscope, and which involves sophisticated processing of the very small and thin tissue to be examined. It is necessary to maintain cleanliness while subjecting the specimen to a multiplicity of different solutions, allowing for these fluid changes, and holding the specimens accessible to said solutions and for subsequent plastic embedding. This invention relates, therefore, to a wide range of dehydrating and impregnating schedules or processes and provides therefor an apparatus that is manually operable and which can be produced and utilized most economically. Although such processes have been conducted both manually and by automation, manual processing with conventional test tubes, beakers and trays is time consuming and wasteful of the solutions, while the automation of such processing is extremely costly and also wasteful of the solutions and accessories such as tubes and containers. With the present invention, the parts of the apparatus are permanent for the most part and are cleaned for reuse, and those parts which are subject to deteriorization or damage are of minimal complexity and are expendable at low cost. In practice, small beakers are employed for containing the solutions employed for fixation, staining etc. to final dehydration and embedding of the biological tissue. Plastic embedding is increasingly used for electron microscopy and the procedures referred to herein therefore require cleanliness, precision and reproducibility, while taking into account the incompatability of solutions with each other and of the viscosities of solutions used in infiltration and embedding.

Conventional laboratory techniques involve the use of test tubes and like vials, made of glass adapted to be sterilized for cleanliness. Heretofore, the specimen to be embedded has been dropped into the test tube so as to rest upon the bottom thereof where it is very much inaccessible for removal, a difficulty involved in ordinary manual processing but obviated in automated processing at the expense of solution waste. However, with the present invention open ended tubes are provided to carry sieve cups that support the specimens to be processed. The cups are easily removed from the tubes for ready access to the specimens which are necessarily very small for ultra thin sectioning. Accordingly, it is an object of this invention to provide a tube and cup combination in place of the conventional test tube or vial, and which allows the ingress and egress of solutions to engulf and receed from the specimen, as may be required.

Conventional laboratory techniques involve the use of beakers and the like, also made of glass adapted to be sterilized for cleanliness. Heretofore, the specimens have been immersed by filling test tubes or vials, trays and/or troughs and the like; with a wasteful volume of solutions. With the present invention, one or more small beakers is employed and means is provided to suspend the aforesaid tube and cup combination therein, for immersion of the specimen by virtue of ingress of solutions through the sieve of the cup. As will be described, the solution level is minimal and immersion of the specimen is nevertheless ensured. Accordingly, it is another object of this invention to provide means carried by the header to place the cups at a determined level for adequate immersion of said specimen. With the present invention, said means is a multi purpose header as will be described, to suspend the tubes, and to provide access to both the beaker and the tubes.

Laboratory procedure involving biological specimens of the type under consideration requires simultaneous processing of a multiplicity of such specimens. Accordingly, it is another object of this invention to provide means by which one or a multiplicity of the tube and cup combinations can be manipulated for subjection to the various solutions and embedding of the specimens supported therein respectively. With the present invention, said means is a base or holder for the one or a multiplicity of sieve cups per se into which the specimens are placed and which subsequently receives the tube or tubes that project upwardly to be suspended by the aforementioned header.

It is still another object of this invention to provide a combination of apparatus as thus far described, the elements of which are assembled and disassembled by light manual pressures, the sieve cup and header elements being fabricated of supple plastic material unaffected by the solutions involved and which press together for reliable integrating when in operation, and readily separable for removal of the specimens for embedding and for cleaning, all as circumstances require.

Having provided for access to the sieve cup, as above described, it is an object to provide for handling thereof and removal of the same from the aforesaid holder, or to replace the same thereon. To this end the tube or tubes are guided by a plate slideable along said tube or tubes to maintain the positions thereof with respect to each other and to the holder and header respectively.

It is an object to assemble as many specimen cups as may be required and to simultaneously handle a multiplicity thereof for processing in relatively small vessels containing the liquids into which specimens carried thereby are to be immersed. In carrying out this invention, the liquid volumes are maintained at a low level and are consequently small while entering the tubes to immerse the specimens by passing through the sieve feature of the cups that support the specimens. Therefore, it is characteristically the raising and lowering of the sieve cups and the orientation of the multiplicity thereof which controls logical processing of numbers of specimens immersed in a plurality of varied liquids used in this preparation for and/or plastic embedding and the like. It is also another feature and an object of this invention to include tooling as part of the apparatus whereby the mesh gradient of the sieve cup is selective as circumstances require, the said tooling involving the cup elements as they are installed in the holder for use.

DRAWINGS

The various objects and features of this invention will be fully understood from the following detailed description of the typical preferred form and application thereof, throughout which description reference is made to the accompanying drawings, in which:

FIG. 1 is a vertical sectional view taken through the specimen processing apparatus.

FIG. 2 is an exploded view of the sieve cup and handling tube.

FIG. 3 is a sectional view taken as indicated by line 3—3 on FIG. 1.

FIG. 4 is an enlarged end view taken as indicated by line 4—4 on FIG. 2.

FIG. 5 is a vertical sectional view of the base holder provided to receive and orient the sieve cups.

FIG. 6 is an exploded perspective view illustrating the sieve cup assembly applied to the base holder, with a handling tube applied, several recesses in the base holder being empty so as to illustrate the fluid interconnection therebetween.

FIG. 7 is a perspective view of the base holder, sieve cup and handling tube assembly, with the index plate applied thereto.

FIG. 8 is a view similar to FIG. 7, with the sieve cup and handling tube assembly removed from the base holder and with the index plate shifted upwardly. And, FIG. 9 is an exploded perspective view of the sieve cup and handling tube assembly with the header applied thereto, in position for entry into a vessel-breaker.

PREFERRED EMBODIMENT

Referring now to the drawings, the apparatus is a manually operable assembly of components combined to serve usefully in the preparation of specimens, especially tissue specimens to be embedded in plastic for viewing in the electron microscope. The processing schedules vary widely for different specimens, a characteristic of the specimens being that they are very small as well as thin and are therefore very delicate. The difficulties experienced with the use of prior art test tubes and vials in the transport of such specimens through the many solutions is obviated with the present invention by providing sieve cups C carried by a multiplicity of numbered handling tubes T coordinated with a base holder B and header H by an index plate P. Assembly of as many sieve cups C as may be required is facilitated by an assembly means or tool A that enables the selection of screen gradients as will be described. The apparatus is therefore adapted to be assembled according to the number of specimens or groups thereof to be processed and the types of liquids into which they are to be immersed.

The apparatus as it will now be described is comprised of the axially related components A, B, C, H, T and P, the combinations of which are multiplied by juxtapositioning thereof preferably within a circular configuration adapted to insertion into cylindrical vessels V such as the standardized laboratory beaker. That is, the said juxtaposed positioning may be that of a pair of axially related combinations, or a group of three or more axially related combinations arranged within a circle; for example, the group of six axially related combinations of components A, B, C, H, T and F shown herein as the preferred embodiment of this invention. In practice, the tubes T are ⅜ inch diameter which rest comfortably in a circular arrangement of six axially related combinations within the confines of a two inch diameter laboratory beaker-vessel V.

The base holder B is a mounting that supports the axially related combination of components that comprise this apparatus, one or more and preferably six units thereof as shown. Further, the base holder establishes the logistic arrangement of specimen positions, identifying them by number, as shown "1, 2, 3, 4, 5, 6". The base holder is sizeable and is adapted to contain a processing solution, being comprised of a body of solid material having a flat bottom 10 for table support and a flat top 11 parallel with and spaced from the bottom. As shown, the body is round with a substantial margin surrounding a group of shallow recesses 13, in this instance a circular series of six recesses or receivers equidistant one from the other and each alike with a cylindrical wall 14 and a concaved bottom 15. The recesses are interconnected by windows 16 to the end that the recesses together form a well for the containment of a process liquid, for example a buffer wash. The recesses or receivers are identical and each opens upwardly at the top 11.

The sieve cups C are interchangeable right cylinders of tube form comprised of outer and inner tube and ring members 20 and 21 with a screen member 22 anchored therebetween. The tube member 20 is shallow and of the same height as the depth of recess 13 and has concentric outer and inner diameter walls and normal opposite open ends, the outer diameter wall fitting free and/or loose within the confines of the reciever wall 14. The ring member 21 is of reduced height and has concentric outer and inner diameter walls and normal opposite open ends, the outer diameter wall telescoping within the inner diameter wall of the tube member 20 with clearance so as to compress the screen member 22 therebetween. As is shown, the screen member 22 extends transversely of and coextensively across the ring member 21 with its outer peripheral margin underlying the lowermost end thereof and turned upward to occupy the interstice-annulus between the tube and ring members dimensioned proportionately to press fit thereover. These three members so assembled comprise a sieve cup.

The assembly means A is provided to establish the above described press fit cup combination, the screen member 22 being available in varied mesh gradients to be selected according to viscosity etc. of the liquids to pass therethrough. The screen members 22 are varied from a fine mesh to a course mesh within a gradient range suitable to the specimens and liquids to be handled, the members 22 being disc-shape circular screen-mesh of soft plastic screen that avoids any specimen damage. In accordance with this invention, the means A is a tool of punch formation, an elongated cylinder with an outer diameter wall of slightly smaller diameter than the inner diameter of tube member 20, and inwardly stepped at 29 to engage the top end of ring member 21 to advance the same into said tube member 20. Accordingly, assembly of the sieve cup C is made by placing a tube member 20 into a recess or receiver 13, and by placing a screen member 22 concentrically thereover upon the top 11 of the base holder B, whereupon the stepped punch tool A carrying the ring 21 is advanced concentrically within the tube member 20 drawing the screen member 22 downward into the anchored position shown with its marginal portion turned upward and pressed between the concentrically telescoped members 20 and 21. The sieve cup assembly C remains loosely fitted within the receiver 13, and ready for the reception of a specimen or specimens and the handling tube T next to be described.

The handling tubes T are interchangeable right cylinders of elongated tube form comprised of outer and inner diameter walls and normal opposite open ends, and each handling tube T identified by a number as shown "1, 2, 3, 4, 5, 6". The outer diameter wall is press fitted into the inner diameter wall of the tube member 20, so as to be manually insertable therein. The handling tubes T are numbered for their logical orientation and identity with respect to the numbered recesses 13, and they are of the same length or height. Accordingly, six numbered handling tubes T establish as many as six vertical columnar extensions of the sieve cups C carried in the receivers 13 of the base holder B.

The index plate P is a relatively thin planar member having a hole pattern complementary to the receiver 13 pattern in the base holder B, in this embodiment six equally spaced openings 35 having a light press fit over the outer diameter walls of the handling tubes T. As shown, the plate P is a circular disc having diametrically opposite and distinguishable notches 36 and 36' to engage complementary keys 37 and 37' on the base holder B for exacting its repeated positioning orienting the same relative to the base holder and tube members. In practice, the index plate P slides onto the handling tubes T so as to orient them for reception of the header H next described, and to subsequently function as a stripper for removal of the handling tubes T with the sieve cups C remaining in their respective recesses or receivers 13.

The header H is a transport means by which a handling tube T and attached sieve cup C can be lifted and moved through successive solutions, or by which a multiplicity of handling tubes T can be simultaneously lifted and moved together through successive solutions. This transport means in the form of header H is part of and carries the axially related combination of components that comprise this apparatus, one or more and for example six units thereof as shown. Further, header H maintains the logistic arrangement of specimen positions, having keys 38 and 38' complementary to and engageable in the notches 36 and 36' in the index plate P. Like the base holder B, the header H is sizeable and is comprised of solid material having a flat top 40 and a flat bottom 41, parallel one with the other. As shown, the header H is round with a substantial margin surrounding a group of connectors 43, either recesses as they are in the base holder B or preferably tapered plugs and in this instance a circular series of six depending plugs equidistant one from the other and each alike with a convergent outer wall formed so as to press fit into the open upper ends of the tubes T respectively. In practice, the tapered plugs are provided with flutes 45 for frictional engagement with the inner diameter walls of the handling tubes T while venting the upper ends thereof to atmosphere. Therefore, the header H with its multiplicity of plugs depending from its bottom 41 is adapted to be simultaneously engaged and disengaged from the multiplicity of handling tubes T, and to transport them from one vessel V to another as required.

Referring now to the vessels V which are to be successively entered into by the transported combinations of tubes T and sieve cups C, it is most practical to employ small laboratory beakers as they are illustrated in the drawings, beakers of right cylinder form having a bottom 45 and upstanding cylinder walls 46, and a rim 47 depressed at its periphery to establish a spout 48. In order to seal the beaker and thereby control evaporation of liquids, the bottom 41 of the header H is form fitted to the configuration of the rim 47 and its spout 48. Further and in order to fill the beaker vessel V, the header body is provided with a filler opening 50 to receive a vacuum tube 51 or stopper 52 therefor centrally located therein as shown. Vacuum infiltration is provided for through the filler opening 50. The group of tubes T and sieve cups C are therefor suspended into the beaker vessel V with the screen members 22 held in close proximity to the bottom 45 of the beaker, whereby but small volume of liquid is required (see FIGS. 1 and 9) for the immersion of specimens supported upon said screen members 22.

From the foregoing it will be seen that the components of this specimen processing apparatus are simple in form so as to be easily manufactured and maintained. In practice, these various components are made of inert materials such as plastic that is impervious to the liquid solutions employed in the specimen processing, for example of "Teflon" or "Nylon". However, it is advantageous to employ a supple and more pliable plastic in the construction of the header H, for example polypropylene. Further, it is preferred that the numbered handling tubes T be made of glass, for cleanliness and its transparency.

A typical step by step manipulation of this apparatus is as follows:

(1) Assemble the tube, ring and screen members of the sieve cups by pressing them into the recesses in the base holder with said tool.

(2) Put fixative or buffer wash in base holder well (when required).

(3) Place tissue specimens in the sieve cups to be supported by said screen members.

(4) Key the numbered index plate onto the top of the base holder.

(5) Press numbered handling tubes into correspondingly numbered index plate openings and into the sieve cups underlying the same.

(6) Raise the index plate upwardly on the tubes so as to position them for receiving the header.

(7) Press the header plugs into the tubes and raise the index plate flush with the bottom thereof.

(8) Put a minimal amount of processing solution into individual beakers and transport the header-tube-sieve cup combination from beaker to beaker according to a time schedule as circumstances require.

(9) Fluid is added or replaced through opening 50.

(10) Vacuum infiltration is applied through opening 50.

(11) Reverse the foregoing procedure for disassembly using the index plate as a stripper to keep the sieve cups in the base holder.

(12) Remove the accessible specimens from each sieve cup by means of a toothpick or applicator stick for subsequent embedding.

Having described only a typical preferred form and application of my invention, I do not wish to be limited or restricted to the specific details herein set forth, but wish to reserve to myself any modifications or variations that may appear to those skilled in the art as set forth within the limits of the following claims:

I claim:

1. A specimen processing apparatus useful in preparing tissue for miscroscopy and the like, and including; a shallow sieve cup comprised of an open ended tube member and a screen member extending coextensively across one end thereof, and an elongated handling tube removably press fitted into the other end of the open ended tube member of the sieve cup, whereby a specimen immersed in liquid entering through the said screen member is accessible thereafter by removal of said handling tube from the shallow sieve cup.

2. The specimen processing apparatus as set forth in claim 1, wherein the screen member is secured coextensively across the one end of the tube member by means of a ring member pressing a peripheral margin of the screen member within an annulus between the tube member and the ring member.

3. The specimen processing apparatus as set forth in claim 1, wherein a screen member of selected mesh gradient is secured coextensively across the one end of the tube member by means of a ring member pressing a peripheral margin of the screen member within an annulus between the tube member and the ring member.

4. A specimen processing apparatus useful in preparing tissue for microscopy and the like, and including; a base holder for apparatus support and having at least one shallow recess opening upwardly, a shallow sieve cup complementing said shallow recess and removably received therein, said sieve cup comprising an open ended tube member and a screen member extending coextensively across one bottom end thereof, and an elongated handling tube removably press fitted into the other top end of the open ended tube member of the sieve cup, whereby a specimen supported upon said screen member is immersed in a liquid contained in said recess and entering through said screen member and is accessible thereafter by removal of said handling tube from the shallow sieve cup.

5. The specimen processing apparatus as set forth in claim 4, wherein the screen member is secured coextensively across the one end of the tube member by means of a ring member pressing a peripheral margin of the screen member within an annulus between the tube member and the ring member.

6. The specimen processing apparatus as set forth in claim 4, wherein a screen member of selected mesh gradient is secured coextensively across the one end of the tube member by means of a ring member pressing a peripheral margin of the screen member within an annulus between the tube member and the ring member.

7. The specimen processing apparatus as set forth in claim 4, wherein the screen member is secured coextensively across the one end of the tube member by means of a ring member pressing a peripheral margin of the screen member within an annulus between the tube member and the ring member, and wherein a removable assembly means forceably positions the ring member within the tube member of the sieve cup.

8. The specimen processing apparatus as set forth in claim 4, wherein a screen member of selected mesh gradient is secured coextensively across the one end of the tube member by means of a ring member pressing a peripheral margin of the screen member within an annulus between the tube member and the ring member, and wherein a removable assembly means forceably positions the ring member within the tube member of the sieve cup.

9. A specimen processing apparatus useful in preparing tissue for microscopy and the like, and including: a header for carrying the apparatus and having at least one connector faced downwardly, a shallow sieve cup comprised of an open ended tube member and a screen member extending coextensively across one bottom end thereof, and an open ended elongated handling tube removably press fitted into the other end of the open ended tube member of the sieve cup and to the connector of the header, whereby a specimen supported upon said screen member is transportable by means of said header through immersion in liquid entering through said screen member and is accessible thereafter by removal of said handling tube from the shallow sieve cup.

10. The specimen processing apparatus as set forth in claim 9, wherein a stripper plate is slideable on the handling tube and engageable with the top end of the tube member of the sieve cup to remove the same from the handling tube.

11. The specimen processing apparatus as set forth in claim 9, wherein an index-stripper plate has an opening for each connector on the header and is slideable on the handling tube and engageable with the top end of the tube member of the sieve cup to remove the same from the handling tube.

12. The specimen processing apparatus as set forth in claim 9, wherein the screen member is secured coextensively across the one end of the tube member by means of a ring member pressing a peripheral margin of the screen member within an annulus between the tube member and the ring member, and wherein a stripper plate is slideable on the handling tube and engageable with the top end of the tube member of the sieve cup to remove the same from the handling tube.

13. The specimen processing apparatus as set forth in claim 9, wherein a screen member of selected mesh gradient is secured coextensively across the one end of the tube member by means of a ring member pressing a peripheral margin of the screen member within an annulus between the tube member and the ring member, and wherein an index-stripper plate has an opening for each connector on the header and is slideable on the handling tube and engageable with the top end of the tube member of the sieve cup to remove the same from the handling tube.

14. The specimen processing apparatus as set forth in claim 9, wherein the header is the closure of at least one vessel containing liquid at a level above the said screen member.

15. The specimen porcessing apparatus as set forth in claim 9, wherein the header is the closure of a vessel, there being a fluid connection therethrough for fluid transfer and vacuumizing.

16. A specimen processing apparatus useful in preparing tissue for microscopy and the like, and including; a base holder for apparatus support and having at least one shallow recess opening upwardly, a shallow sieve cup complementing said shallow recess and removably received therein, said sieve cup comprising an open ended tube member and a screen member extending coextensively across one bottom end thereof, a header for carrying the apparatus and having at least one connector faced downwardly, and an open ended elongated handling tube removably press fitted into the other end of the open ended tube member of the sieve cup and to the header, whereby a specimen supported upon said screen member is transportable by means of said header through immersion in liquid entering through said screen member and is accessible thereafter by removal of said handling tube from the shallow sieve cup.

17. The specimen processing apparatus as set forth in claim 16, wherein a stripper plate is slideable on the handling tube and engageable with the top end of the tube member of the sieve cup to remove the same from the handling tube.

18. The specimen processing apparatus as set forth in claim 16, wherein an index-stripper plate has an opening for each connector on the header and is slideable on the handling tube and engageable with the top end of the tube member of the sieve cup to remove the same from the handling tube.

19. The specimen processing apparatus as set forth in claim 16, wherein the screen member is secured coextensively across the one end of the tube member by means of a ring member pressing a peripheral margin of the screen member within an annulus between the tube member and the ring member, and wherein a stripper plate is slideable on the handling tube and engageable with the top end of the tube member of the sieve cup to remove the same from the handling tube.

20. The specimen processing apparatus as set forth in claim 16, wherein a screen member of selected mesh gradient is secured coextensively across the one end of the tube member by means of a ring member pressing a peripheral margin of the screen member within an annulus between the tube member and the ring member, and wherein an index-stripper plate has an opening for each connector on the header and is slideable on the handling tube and engageable with the top end of the tube member of the sieve cup to remove the same from the handling tube.

21. The specimen processing apparatus as set forth in claim 16, wherein the header is the closure of at least one vessel containing liquid at a level above the said screen member.

22. The specimen processing apparatus as set forth in claim 16, wherein the header is the closure of a vessel, there being a fluid connection therethrough for fluid transfer and vacuumizing.

23. A specimen processing apparatus useful in preparing tissue for microscopy and the like, and including; a base holder for apparatus support and having a multiplicity of shallow recesses opening upwardly therein, a shallow sieve cup complementing each of said shallow recesses and removably received therein respectively, each of said sieve cups comprising an open ended tube member and a bottom screen member extending coextensively across one bottom end thereof, and an elongated handling tube removably press fitted into the other top end of the open ended tube member of each sieve cup, whereby a multiplicity of specimens supported upon said screen members are immersed in a liquid contained in said recesses and entering through said screen members and are accessible thereafter by removal of said handling tubes from the shallow sieve cups.

24. The specimen processing apparatus as set forth in claim 23, wherein each screen member is secured coextensively across the one end of a tube member by means of a ring member pressing a peripheral margin of the screen member within an annulus between the tube member and the ring member.

25. The specimen processing apparatus as set forth in claim 23, wherein each screen member is of selected mesh gradient secured coextensively across the one end of a tube member by means of a ring member pressing a peripheral margin of the screen member within an annulus between the tube member and the ring member.

26. The specimen processing apparatus as set forth in claim 23, wherein each screen member is secured coextensively across the one end of a tube member by means of a ring member pressing a peripheral margin of the screen member within an annulus between the tube member and the ring member, and wherein a removable assembly means positions each ring member within a tube member of the sieve cup.

27. The specimen processing apparatus as set forth in claim 23, wherein each screen member is of selected mesh gradient secured coextensively across the one end of a tube member by means of a ring member pressing a peripheral margin of the screen member within an annulus between the tube member and the ring member, and wherein a removable assembly means positions each ring member within the tube member of the sieve cup.

28. A specimen processing apparatus useful in preparing tissue for microscopy and the like, and including; a header for carrying the apparatus and having a multiplicity of connectors faced downwardly therefrom, a shallow sieve cup complementing each of said seive cups and each comprised of an open ended tube member and a screen member extending coextensively across one bottom end thereof, and an open ended elongated handling tube removably press fitted into the other end of the open ended tube member of each sieve cup and to each complementary connector of the header, whereby a multiplicity of specimens supported upon said screen members are transportable by means of said header through immersion in liquid entering through said screen members and are accessible thereafter by removal of said handling tubes from the shallow sieve cups.

29. The specimen processing apparatus as set forth in claim 28, wherein a stripper plate is slideable on the handling tubes and engageable with the top ends of the tube members of the sieve cups to remove the same from the handling tube.

30. The specimen processing apparatus as set forth in claim 28, wherein an index-stripper plate has an opening for each connector on the header and is slideable on the handling tubes and engageable with the top ends of the tube members of the sieve cups to remove the same from the handling tube.

31. The specimen processing apparatus as set forth in claim 28, wherein each screen member is secured coextensively across the one end of a tube member by means of a ring member pressing a peripheral margin of the screen member within an annulus between the tube member and the ring member, and wherein a stripper plate is slideable on the handling tubes and engageable with the top ends of the tube members of the sieve cups to remove the same from the handling tube.

32. The specimen processing apparatus as set forth in claim 28, wherein each screen member is of selected mesh gradient secured coextensively across the one end of a tube member by means of a ring member pressing a peripheral margin of the screen member within an annulus between the tube member and the ring member, and wherein an index-stripper plate has an opening for each connector on the header and is slideable on the handling tubes and engageable with the top ends of the tube members of the sieve cups to remove the same from the handling tube.

33. The specimen processing apparatus as set forth in claim 28, wherein the header is the closure of each of a series of vessels containing distinctive processing liquids at levels above the said screen members respectively.

34. The specimen processing apparatus as set forth in claim 28, wherein the header is the closure of a vessel, there being a fluid connection therethrough for fluid transfer and vacuumizing.

35. A specimen processing apparatus useful in preparing tissue for microscopy and the like, and including; a base holder for apparatus support and having a multiplicity of shallow recesses opening upwardly therein, a shallow sieve cup complementing each of said shallow recesses and removably received therein respectively, each of said sieve cups comprising an open ended tube member and a screen member extending coextensively across one bottom end thereof, a header for carrying the apparatus and having a multiplicity of connectors faced downwardly therefrom, and an open ended elongated handling tube removably press fitted into the other end of the open ended tube member of each sieve cup and to each complementary connector of the header, whereby a multiplicity of specimens supported upon said screen members are transportable by means of said header through immersion in liquid entering through said screen members and are accessible thereafter by removal of said handling tubes from the shallow sieve cups.

36. The specimen processing apparatus as set forth in claim 35, wherein a stripper plate is slideable on the handling tubes and engageable with the top ends of the tube members of the sieve cups to remove the same from the handling tube.

37. The specimen processing apparatus as set forth in claim 35, wherein an index-stripper plate has an opening for each connector on the header and is slideable on the handling tubes and engageable with the top ends of the tube members of the sieve cups to remove the same from the handling tube.

38. The specimen processing apparatus as set forth in claim 35, wherein each screen member is secured coextensively across the one end of a tube member by means of a ring member pressing a peripheral margin of the screen member within an annulus between the tube member and the ring member, and wherein a stripper plate is slideable on the handling tubes and engageable with the top ends of the tube members of the sieve cups to remove the same from the handling tube.

39. The specimen processing apparatus as set forth in claim 35, wherein each screen member is of selected mesh gradient secured coextensively across the one end of a tube member by means of a ring member pressing a peripheral margin of the screen member within an annulus between the tube member and the ring member and wherein an index-stripper plate has an opening for each connector on the header and is slideable on the handling tubes and engageable with the top ends of the tube members of the sieve cups to remove the same from the handling tube.

40. The specimen processing apparatus as set forth in claim 35, wherein the header is the closure of each of a series of vessels containing distinctive processing liquids at levels above the said screen members respectively.

41. The specimen processing apparatus as set forth in claim 35, wherein the header is the closure of a vessel, there being a fluid connection therethrough for fluid transfer and vacuumizing.

* * * * *